(12) United States Patent
Doerr

(10) Patent No.: US 8,428,721 B2
(45) Date of Patent: Apr. 23, 2013

(54) ADAPTER, ADAPTER RETAIL UNIT AND SYSTEM OF THE ADAPTER, AN IMPLANTABLE MEDICAL ELECTRONIC DEVICE AND AN ELECTRODE LINE

(75) Inventor: Thomas Doerr, Berlin (DE)

(73) Assignee: Biotronik CRM Patent AG, Baar (CH)

( * ) Notice: Subject to any disclaimer, the term of this patent is extended or adjusted under 35 U.S.C. 154(b) by 283 days.

(21) Appl. No.: 12/627,004

(22) Filed: Nov. 30, 2009

(65) Prior Publication Data

US 2010/0137934 A1 Jun. 3, 2010

(30) Foreign Application Priority Data

Dec. 1, 2008 (DE) .......................... 10 2008 044 223

(51) Int. Cl.
*A61N 1/00* (2006.01)
(52) U.S. Cl.
USPC ............................................................. 607/28
(58) Field of Classification Search ...................... 607/37
See application file for complete search history.

(56) References Cited

U.S. PATENT DOCUMENTS

| 5,007,864 A | * | 4/1991 | Stutz, Jr. ........................ 439/651 |
| 5,782,892 A | * | 7/1998 | Castle et al. .................... 607/37 |
| 7,130,699 B2 | * | 10/2006 | Huff et al. ...................... 607/116 |
| 2007/0123949 A1 | * | 5/2007 | Dabney et al. .................. 607/37 |

FOREIGN PATENT DOCUMENTS

| DE | 89 13 339.0 | 11/1998 |
| DE | 10 2007 004 228 | 1/2007 |

OTHER PUBLICATIONS

German Search Report, dated Sep. 14, 2009, 4 pages.

* cited by examiner

*Primary Examiner* — Christopher D Koharski
*Assistant Examiner* — Nadia Ahmad
(74) *Attorney, Agent, or Firm* — ARC IP Law, PC; Joseph J. Mayo

(57) ABSTRACT

An adapter for temporary sterile electric connection of an implantable medical electronic device to an electrode line that is to be connected to the implantable medical electronic device during implantation for undistorted transmission of measured values detectable on the electrode line to the device.

12 Claims, 4 Drawing Sheets

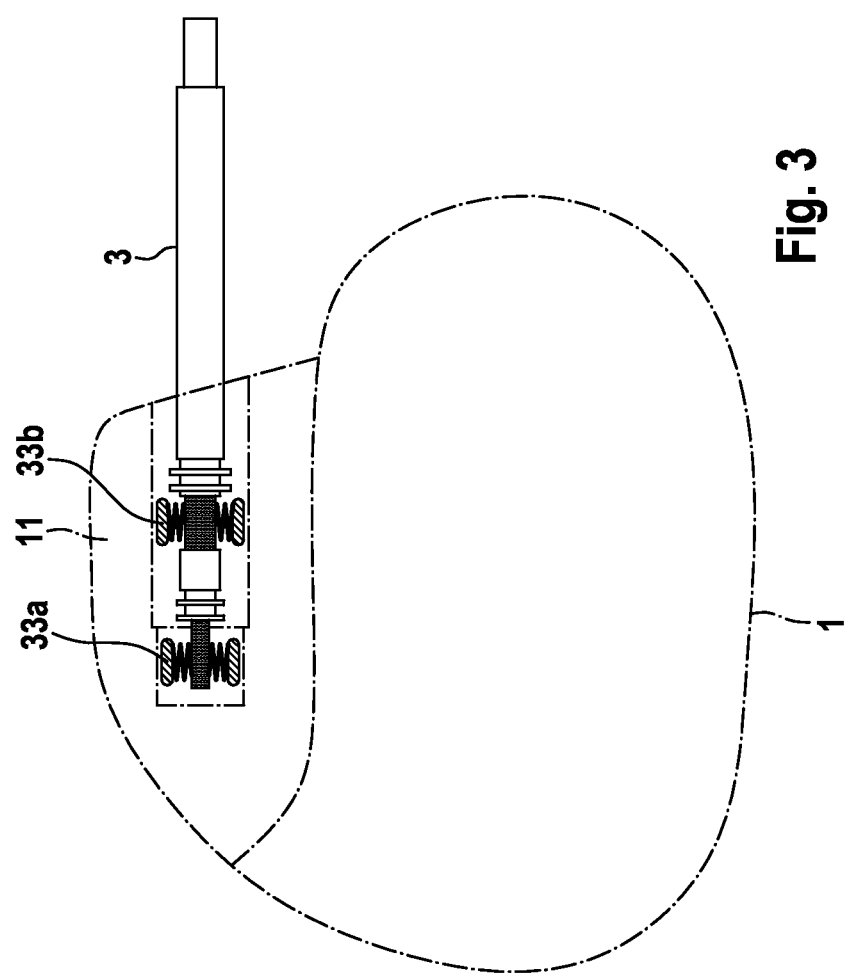

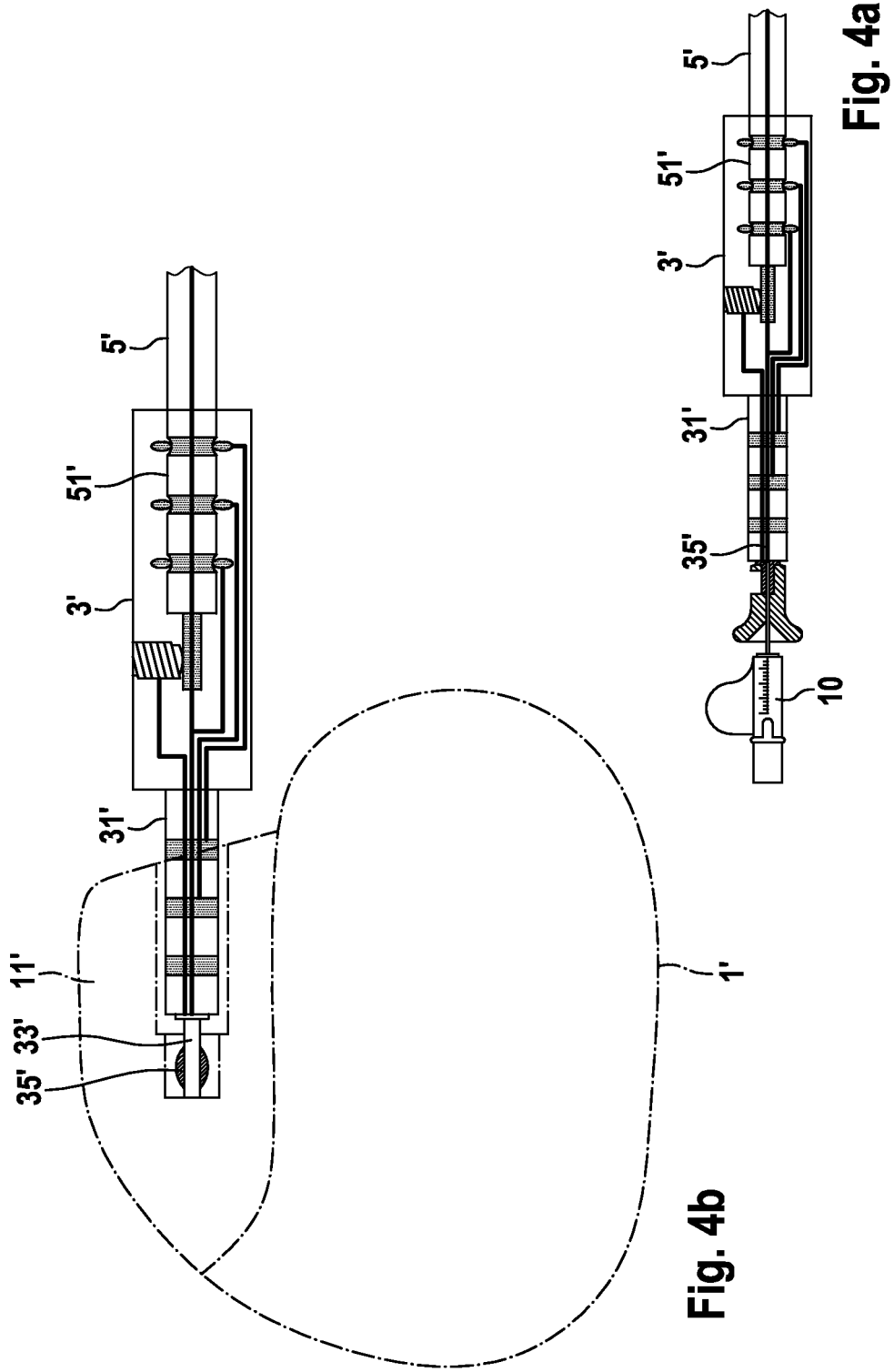

ADAPTER, ADAPTER RETAIL UNIT AND SYSTEM OF THE ADAPTER, AN IMPLANTABLE MEDICAL ELECTRONIC DEVICE AND AN ELECTRODE LINE

This application takes priority from German Patent Application DE 10 2008 044 223.2, filed 1 Dec. 2008, the specification of which is hereby incorporated herein by reference.

BACKGROUND OF THE INVENTION

1. Field of the Invention

The invention relates to an adapter for electric connection of an implantable medical electronic device to an electrode line. It also relates to a retail unit of such an adapter and a system of the adapter, the implantable medical electronic device and an electrode line.

2. Description of the Related Art

Implantable medical electronic devices to support certain body functions such as cardiac pacemakers and implantable defibrillators for supporting cardiac function in pathological cardiac states have been known and have been in clinic use for a long time. In the implanted state (and thus in the use state), an electrode line is permanently connected to these devices to supply electric stimulation pulses or shock pulses, which are generated by corresponding units in the device, to the cardiac tissue, which is at a distance from the device and is to be stimulated.

In the course of implantation of such a device and the respective electrode line, it is necessary to detect certain electric parameters of same and/or body function parameters of the patient by utilizing the electrode line at the respective location of placement of the electrode line. If this yields values which do not lead one to reliably expect permanently satisfactory functions of the overall arrangement, then provisions are to be made for repositioning of the electrode line to a more suitable site of action, and multiple measurements of said parameters are necessary in the course of such repositioning. It is customary during the implantation procedure to connect the electrode line to the required measurement instruments by means of signal lines for this purpose.

With the introduction of long-range RF telemetry for communication between an implantable medical electronic device (hereinafter also referred to as an "electronic implant") and the programming and test device, it is possible to completely omit the wires between the patient and the programming and test device during implantation if measurement of the electrode parameters (e.g., in an ICD implantation: electrode impedance, stimulus threshold, P and R wave amplitudes) is supported completely by the electronic implant during implantation. In these cases, it would be possible to measure all parameters with the implants currently available and to transmit them wirelessly to the programming and test device including the required electrograms.

However, one disadvantage of this approach is the sometimes critical contact between the electrode plugs and the electronic implant, which is repeatedly necessary, because during implantation, the electrodes are measured individually in their implantation series. Furthermore, as already mentioned, the electrodes are repositioned between measurements as necessary. For contacting between the electrodes and the electronic implant, relatively great tightening and untightening forces are required due to the demands made of reliable permanent contact in the implanted states, and a torque screwdriver must be used for tightening and untightening the fixation screws.

In comparison with the traditional electrode measurement, which is performed by wire and allows very simple temporary contacting of the electrodes (by alligator clips or bushings with spring contacts), the complexity of a wireless implant-based measurement having multiple electrodes plugged into the header of the electronic implant is unjustifiably high.

BRIEF SUMMARY OF THE INVENTION

A feature of one or embodiments of the invention is to temporarily and efficiently connect an electronic implant to the electrodes to be implanted for the intraoperative measurement and to do so during the intraoperative measurement, in particular without requiring any tools. This method is comparably simple in comparison with the wired measurement currently being used but it offers the advantage of allowing one to completely eliminate cables between the sterile surgical area and the programming and test device.

The present disclosure provides an adapter for temporary, sterile electric connection of an implantable medical electronic device to an electrode line that is to be connected to the device during implantation for undistorted transmission of measured values detectable on the electrode line to the device. It further provides an adapter retail unit for the adapter and/or the implant, having a sterile package. It also provides a system comprising an electrode line for implantation in a human body, an implantable medical electronic device for use with the electrode line connectable to the device, having measurement means for measuring values detected on the electrode line, such as an electrode impedance, a stimulus threshold or amplitudes of heart-action potentials, and a transmitting unit for wireless transmission of measured values to the outside of the device, and an adapter for temporary, sterile electric connection of the implantable medical electronic device to the electrode line during implantation for undistorted transmission of measured values on the electrode line to the device. For use within a sterile operating field and for wireless transmission of the measured values outward to a location outside of the sterile operating field.

The inventive approach offers the advantage that, in combination with long-range RF telemetry and the measurement functions implemented in the electronic implant, intraoperative testing is made possible by an entirely wireless operation between the programming and test device and the sterile surgical field in the operating room. Contacting of the electrodes is just as simple and efficient as in a hardwired approach. Damage to the electrodes due to multiple plugging and unplugging is prevented. The adapter approach is also less expensive to implement in manufacturing. Likewise, falsification of measurement results due to long wires can be prevented with this method.

Another advantage is that the RF programmer now need not have any galvanic connection to the patient and therefore falls in a different class with regard to the patient lead currents and fault currents. This further reduces the cost of such a programming device in addition to the cost savings for the "implantation module," which is now no longer necessary.

In a preferred embodiment, the proposed system has the following features:

(a) It comprises an electronic implant, which is to be connected to at least one electrode to be implanted for its functional use, whereby it is customary to determine at least one (electric) parameter of the electrode as part of the implantation and to verify the correct placement of the electrode.

(b) The electronic implant has "long-range telemetry," which allows transmission of measured values over a distance of >2 m and is capable of measuring at least one parameter relevant for the electrode placement.
(c) The system has an additional sterile adapter for temporary contacting between the electronic implant and the electrode(s).
(d) The additional adapter is designed so that no tools are needed for contacting and decontacting between the electronic implant and electrode.

According to individual appropriate embodiments of the inventive idea, the proposed approach has one or more of the following features:
(a) The additional adapter is supplied in a sterile package.
(b) The additional adapter is supplied in the sterile package of the electronic implant.
(c) The additional adapter is supplied in the sterile package of the electrode.
(d) The additional adapter is supplied in preassembled form (already inserted into the header of the implant) in the sterile package of the electronic implant.
(e) The additional adapter is supplied in preassembled form in the sterile package of the electrode.
(f) The contacting of the adapter to the electronic implant is accomplished via spring contacts, taking into account the following standards: IS-1, IS-4, DF-1.
(g) The contacting of the adapter to the electrode is accomplished by spring contacts.
(h) The insertion forces for the adapter into the electronic implant do not exceed 14 decanewtons.
(i) The extraction force for the adapter from the electronic implant does not exceed 14 decanewtons.
(j) The implant is capable of measuring all parameters for the electrode placement required for the particular application.
(k) The implant has RF telemetry.
(l) The implant has RF telemetry in the MICS band.

BRIEF DESCRIPTION OF THE DRAWINGS

Advantages and expediencies of the present invention are also derived from the following description of exemplary embodiments with reference to the figures, in which:
FIG. 3 shows a detailed diagram of the fixation of an inventive adapter in the header of a cardiac pacemaker, which represents the implantable device,
and
FIGS. 4a and 4b show views of another embodiment of an arrangement having an inventive adapter;
FIG. 4a shows an electrode line end with the adapter attached during insertion,
and FIG. 4b shows the adapter in the use state.

DETAILED DESCRIPTION OF THE INVENTION

Figure 1:
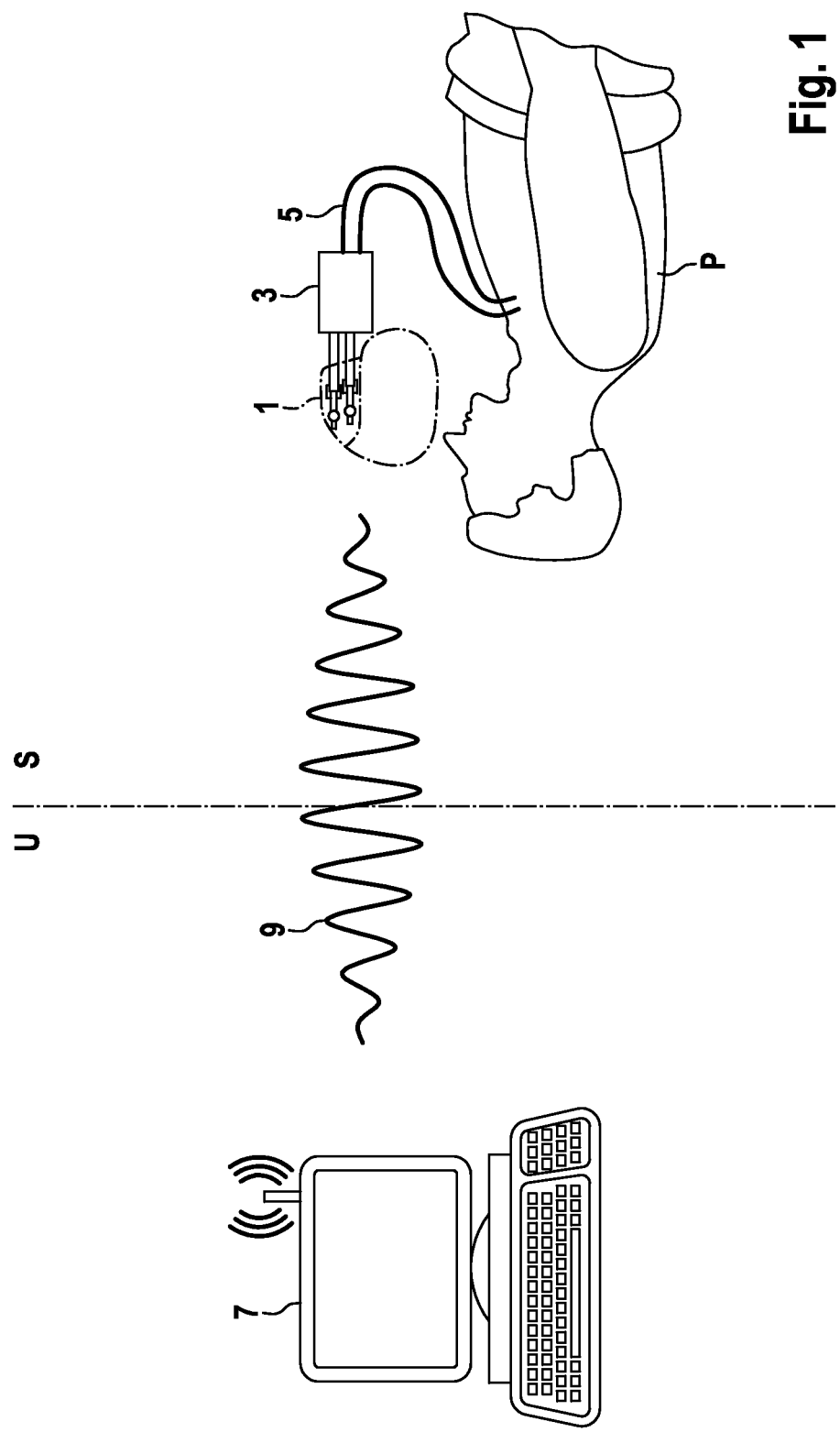
FIG. 1 shows a schematic overall diagram of an inventive system.

FIG. 1 shows an overall system consisting of a cardiac pacemaker 1, an electrode adapter 3 for temporary contacting of an implantable electrode line 5 and the programming and test device 7. In this design, the programming and test device is in an unsterile area U in the operating room. The electrodes implanted in patient P, the cardiac pacemaker 1 and the electrode adapter 3 are arranged as sterile components in the sterile area S of the operating room. The control and data transmission of the intraoperative measurements, e.g., P and R wave amplitudes, stimulation thresholds, electrode impedances, are accomplished by means of RF telemetry 9.

Figure 2:
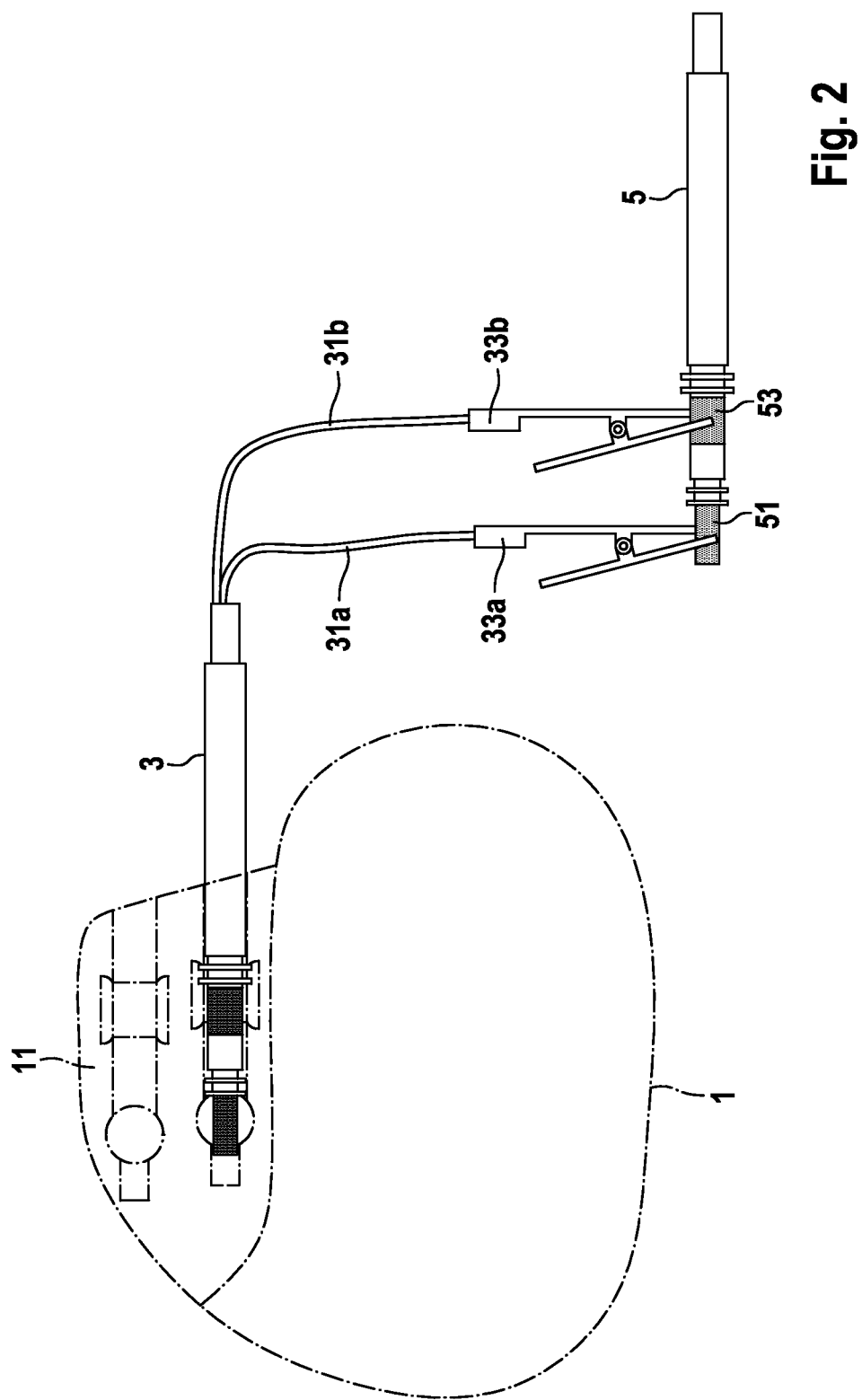
FIG. 2 shows a schematic diagram of one embodiment of the inventive system.

FIG. 2 shows a simple embodiment of the adapter 3 for temporary electrode contacting, where an IS-1 plug (alternatively IS-4, DF-1) is already contacted in the header 11 at the time of delivery of the cardiac pacemaker 1. This adapter carries the electric connections by means of two cables 31a, 31b to two alligator clips 33a, 33b and thus allows simple contacting of the electrode line to be tested by clamping the alligator clips on their plug contacts 51, 53.

FIG. 3 shows a detail of the embodiment of the preassembled electrode adapter 3. It shows the contacting of this adapter by means of spring contacts 33a, 33b in the header 11 of the cardiac pacemaker 1. With this arrangement, after the end of the intraoperative measurements, it is possible to remove the adapter without the use of tools by simply pulling it out of the header using a moderate extraction force.

FIGS. 4a and 4b show an electrode adapter 3' as an alternative embodiment. In this embodiment, the adapter is not supplied together with the electronic implant but instead is preassembled on the plug 51' of an electrode line 5' to be implanted.

In this example, a 4-polar electrode is shown. The electrode adapter 3' is attached to the plug 5' of this electrode line by means of spring contacting in accordance with the IS-4 standard, this in turn comprising an IS-4 plug 31' whose pin 33' includes a spring contact 35' for contacting in the header 11' of the cardiac pacemaker V. In addition, the diameter of the adapter plug 31' is designed to be at the lower tolerance limit or slightly below the dimensions defined in the IS-4 standard, so that the plugging and unplugging forces turn out to be lower with respect to the electrode. Repeated contacting is thus readily possible and does not require tools.

Furthermore, this adapter has a central borehole 35' for insertion of a mandrel 10 for implantation of the electrode, so this adapter need not be removed for electrode implantation. The mandrels assigned to the electrode are lengthened accordingly by the length of the adapter.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

What is claimed is:
1. An adapter for temporary, sterile electric connection of an implantable medical electronic device to an electrode line that is to be connected to the implantable medical electronic device during implantation comprising:
a plug section comprising a smaller diameter than a standard diameter of a standard plug section of an electrode line, said plug section having at least one external contact wherein said plug section is configured to plug into a header of an implantable medical electronic device so that plugging and unplugging forces are lower with respect to plugging or unplugging said electrode line in said header of said implantable medical electronic device;
at least one electrical line coupled with said at least one external contact wherein said at least one electrical line is configured to extend to an opposing side of said adapter with respect to said plug section and wherein said at least one electrical line is configured to couple with said electrode line implanted in a patient;
wherein said at least one external contact is configured to transmit measured values that are detectable on the electrode line to the implantable medical electronic device wherein said implantable medical electronic device is configured to wirelessly transmit said measured values to a programming unit in an unsterile environment; and, wherein said plug section is configured to connect to the implantable medical electronic device as well as to the electrode line without tools and wherein said plug section is configured so that no more than 14 decanewtons of force is required to insert or extract said plug section into or out of said a header of said implantable medical electronic device.

2. The adapter according to claim 1, further comprising:
a plug-receiving section configured to receive the plug section of the electrode line, said plug-receiving section having at least one internal contact;
wherein the at least one external contact is connected to the at least one internal contact that corresponds to the at least one external contact via at least one signal line;
a first fixation element configured for detachable fixation of the adapter to the implantable medical electronic device; and,
a second fixation element configured for detachable connection of the adapter to the electrode line.

3. The adapter according to claim 1,
wherein said plug section further comprises at least one signal cable;
a first fixation element configured for detachable fixation of the adapter on the implantable medical electronic device;
a second fixation element configured for detachable connection of the adapter to the electrode line; and,
wherein the second fixation element is configured as a clamp contact configured to fix the at least one signal cable on at least one contact of the plug section of the electrode line.

4. The adapter according to claim 1, further comprising a first fixation element configured for detachable fixation of the adapter to the implantable medical electronic device wherein the first fixation element comprises spring contacts configured to IS-1, IS-4, or DF-1 standards, wherein said first fixation element is configured for fixation in the header of the implantable medical electronic device.

5. The adapter according to claim 1 further comprising an adapter retail unit comprising a sterile package.

6. The adapter retail unit according to claim 5, wherein the sterile package also contains the electrode line to which the adapter is configured to couple with.

7. The adapter retail unit according to claim 6, wherein the adapter is preassembled with the electrode line.

8. The adapter retail unit according to claim 5, wherein the sterile package also contains the implantable electronic device to which the adapter is configured to couple with.

9. The adapter retail unit according to claim 8, wherein the adapter is preassembled with the implantable medical electronic device.

10. The adapter according to claim 1 in combination with and further comprising an implantable medical electronic device wherein said implantable medical electronic device comprises:
a measurement element configured to obtain measured values that are detected on the electrode line, wherein said measured values comprise electrode impedance, a stimulus threshold or amplitudes of heart-action potentials; and,
a transmission unit configured to wirelessly transmit said measured values outside of the implantable medical electronic device.

11. The implantable medical electronic device according to claim 10, wherein the transmission unit has a transmitter range of two meters or more.

12. The implantable medical electronic device according to claim 10, wherein the transmission unit is configured as an RF telemetry unit, which operates in an MICS band.

* * * * *